United States Patent [19]

Debat et al.

[11] 4,151,278

[45] Apr. 24, 1979

[54] **PROCESS FOR THE PREPARATION OF AN EXTRACT OF *TEUCRIUM MARUM* USED IN PARTICULAR IN THERAPY**

[75] Inventors: Jacques Debat, Saint Cloud; Jean Lemoine, Garches; Bernard Guay, Saint Cloud; Claude Crescioni, Garches, all of France

[73] Assignee: Institut de Recherches Chimiques et Biologiques Appliquees, Paris, France

[21] Appl. No.: 842,364

[22] Filed: Oct. 14, 1977

[30] Foreign Application Priority Data

Oct. 15, 1976 [GB] United Kingdom ............... 43043/76

[51] Int. Cl.$^2$ ..................... A61K 35/78; C07G 17/00
[52] U.S. Cl. .................................. 424/195; 260/236.5
[58] Field of Search ....................... 424/195; 260/236.5

[56] References Cited

U.S. PATENT DOCUMENTS 3,856,946  12/1974  Debat .................................. 424/195

OTHER PUBLICATIONS

Clark, A Dictionary of Practical Materia Medica, vol. II, published by The Homoeopathic Pub. Co., London (1902), pp. 1401–1405.
Chemical Abstracts vol. 47:822e; vol. 29:15784; vol. 28:6243[7] & vol. 85: 108787f.

*Primary Examiner*—Donald B. Moyer
*Attorney, Agent, or Firm*—Brooks, Haidt, Haffner & Delahunty

[57] ABSTRACT

The present invention relates to a process for the preparation of an extract of *Teucrium marum* used in therapy, according to which the whole plant, or part of the plant, is subjected to a treatment with a solvent, the said process being characterized in that the said treatment is carried out with a solvent chosen from among the group comprising boiling water in the presence of NH$_3$, pentane, hexane, heptane, cyclohexane, cyclopentane, petroleum ether, methylene chloride and mixtures of these, and in that, if necessary, the resulting extract is subjected to a purification.

14 Claims, 1 Drawing Figure

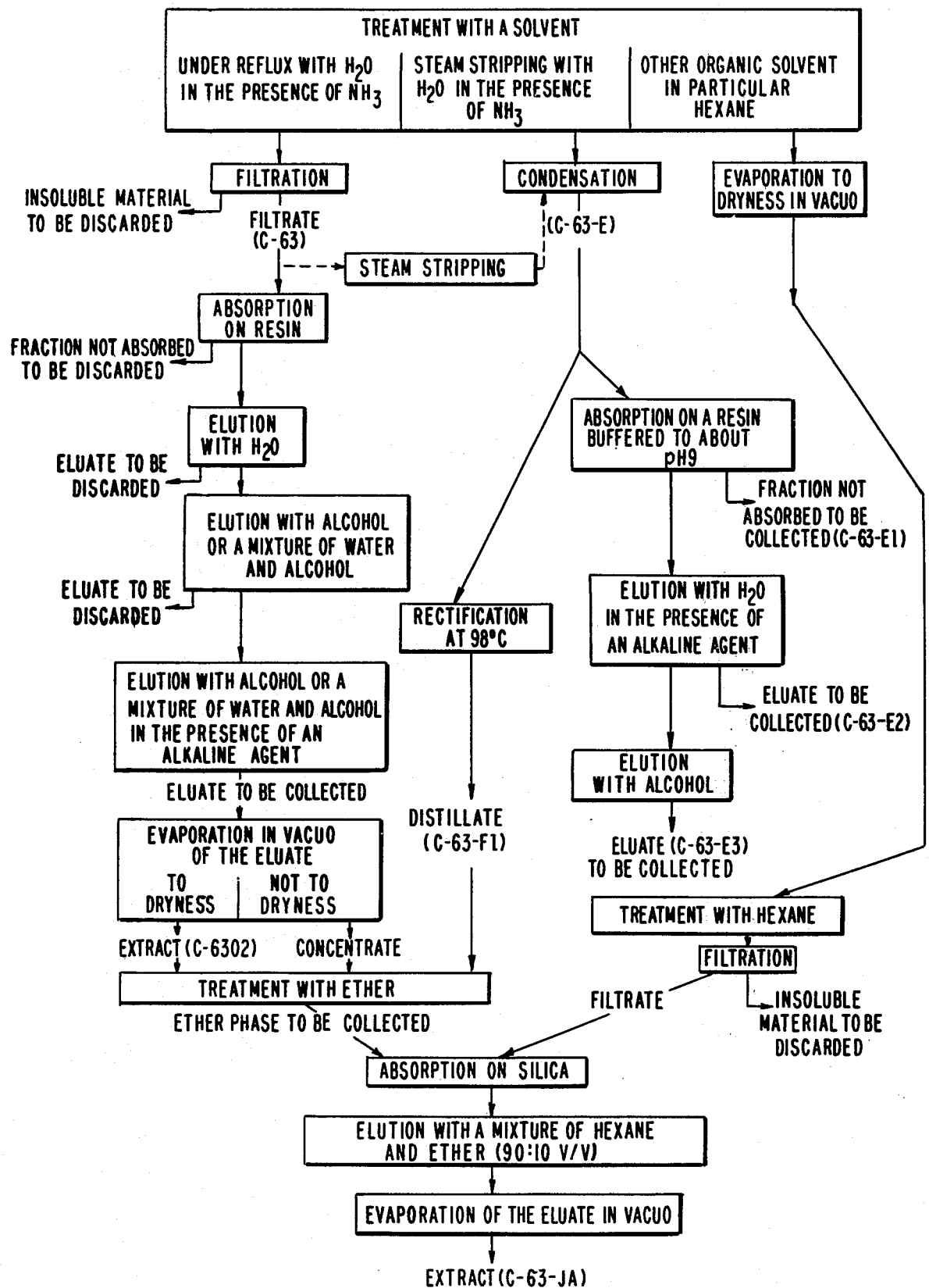

PROCESS FOR THE PREPARATION OF AN EXTRACT OF TEUCRIUM MARUM USED IN PARTICULAR IN THERAPY

The present invention relates to a new process for the preparation of a purified extract of *Teucrium marum*. The said purified extract is a new industrial product which can in particular be used in therapy.

It is known that *Teucrium marum*, also called "cat thyme" or "sea germander", is a shrub which belongs to the sub-category of the gamopetalous plants, of the family of the Labiatae, and grows in particular in Corsica. This plant, which has compactly petiolated entire leaves which are white and woolly underneath, purplish flowers, a villous calix with almost equal teeth which do not reach half the size of the calix, a villous fruit and an ethereal odour (which causes the plant to be sought out by cats) has in particular been described by G. GARNIER et al. in "Ressources Médicinales de la Flore Francaise" ("Medicinal Resources of the French Flora"), Volume II, published by Vigot, Paris (1961). It is also known that it has in the past been proposed to use this plant in therapy, in particular in the form of an infusion (that is to say an extract obtained by treating the plant with hot water, at about 60° C.).

The invention relates to the production of an extract of *Teucrium marum* which is useful in therapy, especially as an antispasmodic agent and respiratory analeptic agent.

The process of extraction according to the invention, according to which the entire plant (that is to say the stems, the leaves, the floral apices, the fruit and the roots), or part of the plant, is subjected to a treatment with a solvent, is characterised in that the said treatment is carried out with a solvent chosen from amongst the group comprising boiling water in the presence of $NH_3$, pentane, hexane, heptane, cyclohexane, $CH_2Cl_2$, cyclopentane, petroleum ether and mixtures of these, and in that, if necessary, the resulting extract is subjected to a purification.

The invention is further illustrated by reference to the accompanying FIGURE, which is a schematic diagram of the process of the present invention.

It is proposed that the said treatment can advantageously be carried out by using, per litre of solvent, an amount of 30 to 150 g of ground and dry plant, the preferred amount of ground and dry plant per litre of solvent being 100 g.

Chloroform can also be used in order to carry out this treatment. However, an experiment shows that this solvent is of no value from an industrial point of view. In fact, it solubilizes substances contained in the plant which do not exhibit the desired antispasmodic and respiratory analeptic properties. The use of chloroform has not therefore been singled out, because it entails expensive secondary treatments in order to remove the said substances.

Methylene chloride, which does not exhibit all the disadvantages, can be used according to the process of the invention; however, as it leads to lower yields, either boiling water in the presence of $NH_3$ (4 to 10 g of $NH_3$ per litre of water), or pentane, hexane, heptane, cyclohexane, cyclopentane, petroleum ether or mixtures of these, is more preferably used, the best solvent from an industrial point of view being hexane.

The treatment with a solvent can be carried out in accordance with four variants, the first three variants relating to the use of boiling water in the presence of $NH_3$, and the fourth variant relating to the use of another solvent according to the invention, namely:

Variant A: treatment under reflux, followed by filtration to collect the resulting aqueous solution;

Variant B: steam stripping, followed by condensation to collect the resulting condensate;

Variant C: treatment under reflux, filtration, steam stripping of the resulting aqueous solution, and subsequent condensation; and Variant D: treatment with an organic solvent, followed by concentration of the resulting solution.

According to variant A, the treatment with water in the presence of $NH_3$ is carried out under reflux for about 2 hours, after which it is advantageous to leave the reaction mixture to undergo maceration for about 24 hours at ambient temperature (15°–25° C.).

According to variant B, the treatment is stopped when the condensate collected has a volume equal to at most 2,500 ml; in practice, the said treatment is stopped when a condensate of 500 to 2,500 ml has been collected. Variant C, which combines variants A and B, gives results equivalent to variant B from the point of view of therapeutic activity. In the text which follows, the extract obtained according to variant A is referred to as complete aqueous extract of *Teucrium marum*.

According to variant D, the extraction is carried out by means of a Soxhlet apparatus; after filtration to remove insoluble material, the filtrate is concentrated to dryness under reduced pressure.

The purification of the extract, obtained either by treatment with boiling water in the presence of $NH_3$, or perfectly with an organic solvent such as defined above, can be carried out according to a method which is in itself known. The purification proposed according to the invention comprises fixing the said extract on a carrier and then eluting by means of one or more eluting agents.

More precisely, the method of purification of the aqueous extract obtained according to variant A is characterised in that the following are carried out:

(a) the aqueous solution is subjected to an absorption on resin, the fraction not absorbed on the resin after passing over the latter being discarded;

(b) the resin is then washed with distilled water until the rinsing water, which is discarded, is colourless;

(c) the resin washed in this way, to which the product to be collected is fixed, is subjected to elution with an alcohol or a mixture of water and alcohol until the eluate, which is discarded, is colourless;

(d) the resin treated in this way, to which the product to be collected is fixed, is subjected to an elution with an alcohol or a mixture of water and alcohol, in the presence of an alkaline agent, until the resulting eluate is colourless;

(e) the eluate obtained in stage (d) is subjected to an evaporation in vacuo; and then, if necessary, (f) the residue from evaporation obtained in stage (e) is subjected to a treatment with ether, and the ether phase is collected and concentrated in vacuo;

(g) the concentrate obtained in this way is subjected to an absorption on silica;

(h) the silica treated in this way is subjected to an elution with a mixture of hexane and ether (90:10 v/v); and (i) the eluate obtained in this way is concentrated to dryness in vacuo in order to achieve a dry product (which is in the form of a powder).

The absorption of stage (a) is carried out using a macromolecular resin, for example a crosslinked polystyrene ion exchange resin, marketed under the name of "Amberlite XAD2".

The alcohols used in stages (c) and (d) are lower alkanols, such as methanol, ethanol and propanol; the mixtures of water and alcohol contain at least 90% by volume of one of the lower alkanols mentioned above. The preferred eluant in stages (c) and (d) consists of ethanol or a mixture of water and ethanol in the volume ratio of 4:96.

The alkaline agent of stage (d) can in particular be chosen from amongst NaOH, KOH and $NH_3$. It will be seen in Example 2 below that the preferred alkaline agent is $NH_3$ used at a concentration of 30 g/l of eluent.

The evaporation in vacuo, in stage (e), is carried out at 60° C. If it is not desired to continue the purification, this evaporation is carried out until a dry product is obtained. On the other hand, if it is desired to continue the purification according to stages (f) to (i), the treatment with ether in stage (f) can be carried out either on the said dry product or on a residue from evaporation which has been concentrated in vacuo.

In stage (f), the ether used can be dimethyl ether or diethyl ether. The use of diethyl ether, from which peroxide has been removed, is advantageously proposed.

Two methods of purification of the extracts obtained according to variants B and C are possible, the second method being preferred because it is more practical.

The first method of purification of the extract obtained according to either one of variants B and C is characterised in that the following are carried out successively:

($a_1$) the condensate is subjected to an absorption on a resin buffered to about pH 9, the fraction not absorbed on the resin after passing over the latter—this being the fraction which is useful in therapy—being collected;

($b_1$) the resin treated in this way is subjected to an elution with an alkaline agent, especially 1N NaOH or 1N KOH, and a first eluate which is useful in therapy is collected; and ($c_1$) the resin is subjected to an elution with a lower alkanol, especially ethanol, and a second eluate which is useful in therapy is collected.

The resin used in stage ($a_1$) is preferably a solid resin, for example a crosslinked polystyrene ion exchange resin, marketed under the name of "Amberlite IRC-50". This resin is buffered to about pH 9 before passing the condensate over it; for example, it can in particular be buffered to pH 9.1 with a buffering agent such as 0.02 M sodium borate.

The second method of purification of the extract obtained according to either one of variants B and C is characterised in that the condensate (which has been obtained by steam stripping) is subjected to a rectification at 98° C. (under a pressure of 1 atmosphere), and the rectified fraction is collected and then treated according to the details in stages (f) to (i) above. The final product obtained according to this method is identical to that obtained in stage (i) of the purification of the extract of variant A.

The method of purification of the extract obtained according to variant D is characterised in that the following are carried out successively: the dry product (which has been obtained by evaporation in vacuo of the solvent used in the treatment) is redissolved in hexane, the solution is filtered to remove the insoluble material, the filtrate obtained in this way is subjected to an absorption on silica, it is eluted with a mixture of hexane and ether (90:10 v/v), and the eluate obtained in this way is evaporated to dryness in vacuo.

In this last method, the absorption on silica, the elution and the evaporation to dryness of the eluate are carried out according to the details in stages (g) to (i). The final product is also identical to that obtained in stage (i) of the purification of the extract of variant A.

The process of extraction and purification according to the invention has been summarised in diagram I given later.

Other advantages and characteristics according to the invention will be better understood on reading the preparation examples which follow and which are given by way of illustration and without implying any limitation.

EXAMPLE 1

Preparation of the total aqueous extract

The whole plant of *Teucrium marum*, dried in an oven at 37° C. and ground, is subjected to an extraction with distilled water under the following conditions:

3 l of distilled water are added to 300 g of plant and the water is brought to the boil; 10 ml of $NH_4OH$, containing 20% of $NH_3$, are added before boiling starts. The solution is then boiled under reflux for 2 hours, after which the material is left to undergo maceration at ambient temperature for 20 hours. The extract is then filtered through a fluted filter so as to recover the aqueous solution.

The aqueous solution thus obtained constitutes the complete aqueous extract of *Teucrium marum* which has been coded "C-63" in the pharmacological experiments given later.

EXAMPLE 2

Purification of the complete aqueous extract

The aqueous solution obtained in Example 1 is subjected to absorption chromatography on resin. The resin used is an insoluble polymer, namely, in this case, a crosslinked polystyrene (Amberlite XAD-2); this resin is used to pack a column of 5 cm internal diameter and 60 cm height, the wet weight of resin used being 1,200 g and the aqueous solution being passed over the resin at a speed of 10 ml/minute.

The fraction (fraction A-I) which is not absorbed after passing over the resin is discarded. The resin is then rinsed with distilled water until the rinsing water collected at the bottom of the column is colourless. This rinsing water is discarded.

Elution is thereafter carried out:

(1) with a 96:4 mixture of ethanol and water, until the eluate is colourless; a second fraction (called fraction A-II) is thus obtained, which is discarded; and (2) with a 96:4 by volume mixture of ethanol and water containing 30 g/l of $NH_3$, until the eluate is colourless; a third fraction is thus collected (called fraction A-III) which is reduced to dryness by evaporation under reduced vacuum (sic—? reduced pressure or ? vacuum), using a rotary evaporator at 60° C.

The yield of final product is 6% by weight relative to the weight of the dry plant used as starting material.

The product obtained by evaporation of fraction A-III in vacuo in accordance with the details of the preceding example has been coded "C-6302" and subjected to analytical and pharmacological tests.

ANALYTICAL CHARACTERISTICS

Chromatography on a thin layer of silica [using, as the mobile phase, a mixture of chloroform, ethanol and diethylamine in the volume ratio of 95:4:1] of fraction III, on the one hand, and of product C-6302, redissolved in the 96:4 mixture of ethanol and water, on the other, gives the same three spots, namely:

Spot No.1, Rf=0.71, revealed under a lamp emitting ultraviolet of wavelength 254 nm, Spot No.2, Rf=0.80, revealed in a mauve-blue colour by spraying with a mixture of 1 ml of $H_2SO_4$, 300 mg of vanillin and 10 ml of ethanol, and heating in an oven at 110° C; and Spot No.3, Rf=0.87, revealed in grey-blue by the preceding reactant.

EXAMPLE 3

Vapour stripping 150 g of the whole plant of *Teucrium marum*, which has been dried in an oven at 37° C. and ground, are suspended in 4 l of distilled water and the suspension is brought to the boil. Steam stripping is carried out. The vapours are condensed by cooling and collected until the volume reaches 2,500 ml.

The extract thus obtained has hereinafter been referred to under code number "C-63-E".

EXAMPLE 4

Purification of the extract obtained by steam stripping

The product obtained according to Example 3 was subjected to absorption chromatography. The resin used is an insoluble polymer consisting of a crosslinked polystyrene marketed under the name of "Amberlite IRC-50". A column of 25 mm internal diameter is packed with "Amberlite IRC-50" to a height of 30 cm and provided, at its outlet, with a recording device coupled to a U.V. cell (so as to know the absorption of the eluate from the column, especially at a fixed wavelength of 270 nm).

The resin is then buffered with 0.02 M sodium borate to pH 9.1 until the column eluate has an equivalent pH. The "C-63-E" extract is then absorbed on the resin at a speed of 3 ml/minute.

A first fraction (called "B-I" and coded "C-63-El"), which is not absorbed after passing over the resin, is collected; it contains an odoriferous constituent.

When this first fraction has been collected, an elution is carried out with 140 ml of 1N NaOH. A second fraction (called "B-II" and coded "C-63-E2") is collected.

Thereafter, a fresh elution is carried out with anhydrous ethanol and a third eluted fraction (called "B-III" and coded "C-63-E3") is collected.

N.B. Though the experiments given below were carried out with fractions B-I, B-II and B-III obtained as above, and optionally diluted with water, it is possible, if necessary, to concentrate the fractions under reduced pressure before using them.

SPECTROSCOPIC ANALYSIS

The spectroscopic analysis was carried out on a Perkin-Elmer apparatus. The "C-63-E" extract exhibits absorption peaks in its U.V. spectrum at 200 nm, 225 nm, 262 nm, 268 nm and 280 nm. The "C-63-E1" and "C-63-E2" extracts exhibit absorption peaks at 200 nm, 225 nm and 280 nm. The "C-63-E3" extract exhibits absorption peaks at 200 nm, 262 nm and 268 nm.

CHROMATOGRAPHIC ANALYSIS

Chromatography, on a thin layer of silica, of the extracts "C-63-E" and "C-63-E3", using, as the mobile phase, a mixture of chloroform, methanol and water in the volume ratio of 40:45:15, gives the same two spots, namely:

a first spot of Rf=0.65 and a second spot of Rf=0.75, both these spots being revealed:

in orange, by Draggendorf's reagent, followed by heating in an oven at 110° C., in mauve, by Marquis' reagent, followed by heating in an oven at 110° C. for 10 minutes, and in yellow, on a violet background, by iodoplatinate reagent.

EXAMPLE 5

The procedure indicated in Example 3 is followed, with the difference that only the first 500 millilitres of condensates are collected. An extract is obtained which is identical to the "C-63-E" extract from the spectroscopic and chromatographic point of view and which has the advantage of being more concentrated than the "C-63-E" extract of Example 3, and is hence more valuable in that it is possible to avoid subjecting it to a concentrating operation.

The examples which follow refer to the production of the extract of Teucrium marum which is preferred from the point of view of therapy. Example 6 describes the best method of preparation of the said extract.

EXAMPLE 6

(a) Preparation according to method D 400 g of ground and dried plant are extracted with 4 l of hexane in a Soxhlet apparatus. The insoluble material is discarded and the hexane solution is evaporated to dryness under reduced pressure to obtain a dry extract.

(b) Purification

The dry extract is taken up in hexane. The amount of hexane to be used for this purpose is 1 volume per 10 volumes of the solvent as the preceding treatment, this being 400 ml of hexane in the present case. The solution is filtered to remove the insoluble material and the filtrate is poured onto an absorption column packed with silica. An elution is carried out with a mixture of diethyl ether and hexane (90:10 v/v). The eluate is then concentrated under reduced pressure and a pulverulent final extract (2.3 g), referred to hereafter under code number "C-63-JA", is obtained by evaporation to dryness; it has the following analytical characteristics:

THIN LAYER CHROMATOGRAPHY

C-63-JA gives a spot revealed in a mauve-blue colour, of Rf 0.45 under the following operating conditions:

| | |
|---|---|
| support: | silica |
| mobile phase: | chloroform |
| developer: | sulphuric acid - vanillin (1 g of vanillin per 100 ml of concentrated sulphuric acid of density 1.84). |

GAS-LIQUID CHROMATOGRAPHY

Under the following operating conditions:

| | |
|---|---|
| column: | 50% of carbowax 20M length: 182.8 cm (6 feet) |
| injection temperature: | 250° C. |
| detection temperature: | 250° C. |
| carrier gas: | nitrogen |
| temperature programme: | from 100° to 200° C. at the rate of 4° C. per minute, |

C-63-JA gives two peaks, the retention times, expressed in cm, being 7.75 cm for the 1st peak and 8.35 cm for the second peak.

Infra-red spectrum

C-63-JA exhibits three absorption bands:
2,700–3,000 cm$^{-1}$ (aldehyde function)
1,700–1,730 cm$^{-1}$ (ketone function)
1,380–1,460 cm$^{-1}$ ($CH_2$ or $CH_3$ group)

For the pharmacological tests, C-63-JA is used dissolved in a mixture of water and ethanol (95:5 v/v).

EXAMPLE 7

Purification of the extract obtained by steam stripping 100 ml of the condensate obtained in Example 3 is subjected to a rectification at 98° C. 40 ml of unrectified residue are obtained, which are discarded, and 60 ml of distillate are divided into 6 fractions each of 10 ml. The first two fractions, which contain the greater part of the active substance of *Teucrium marum,* are combined and extracted with diethyl ether from which peroxide has been removed (at a rate of 3 volumes of ether per volume of distillate). The ether phase is collected and concentrated in vacuo at a temperature which is less than or equal to 30° C. (By evaporating to dryness, the extract coded C-63-F1 is obtained.) As indicated in Example 6, the resulting concentrate is absorbed on a silica column and eluted and, after the eluate has been evaporated to dryness in vacuo, a therapeutically active pulverulent substance is obtained which, after analysis, was shown to be identical to extract C-63-JA.

EXAMPLE 8

Purification of the total aqueous extract

Extract C-6302 obtained in Example 2 is taken up in ether. The ether used is diethyl ether from which peroxide has previously been removed. An ether phase is obtained which is concentrated in vacuo at a temperature which is less than or equal to 30° C. The resulting concentrate is poured onto a silica column, an elution is then carried out, and the eluate is evaporated to dryness under reduced pressure to obtain a therapeutically active pulverulent substance which, after analysis, was shown to be identical to extract C-63-JA.

Extract C-63-JA is obtained by following the procedure indicated in Example 8, but by using fraction A-III obtained in Example 2 and by only retaining the ether phase.

PHARMACOLOGICAL TESTS

Toxicity

The toxicity test was carried out on male mice weighing 20 g, grouped into batches of twenty animals, administration being carried out intravenously, intraperitoneally and orally. The corresponding results have been listed in Table I. In this table, the doses used are expressed as the weight of plant starting material required to obtain the various extracts, taking the extraction used into account.

| | Toxicity expressed in g of plant | | |
|---|---|---|---|
| Extracts | intraperitoneal administration | intravenous administration | oral administration |
| C-63 | 20 g/kg: no fatality | 20 g/kg: no fatality | — |
| C-63-E | 12 g/kg: no fatality | 12 g/kg: 40% fatality 6 g/kg: 30% fatality 3 g/kg: 30% fatality | 12 g/kg: no fatality |
| C-63-F1 | — | LD 50 = 2 g/kg | — |
| C-63-JA | — | LD 50 = 1.2 g/kg | — |

Antispasmodicaction "in vitro"

The results obtained with "C-63", "C-6302" and "C63-JA" extracts with regard to the antispasmodic action, which were obtained on the isolated ileum of guinea pigs (with regard to a possible antihistamine effect), on the isolated duodenum of rats (with regard to anticholinergic and anti-$BaCl_2$ effects) and on the isolated uterus of rats (with regard to the antiserotonin effect) have been summarised below.

The working procedures were as follows:

(a) The isolated ileums of guinea pigs are obtained by the Magnus technique: the guinea pigs are killed by breaking their neck and are then bled. A length of ileum of about 1 to 2 cm is removed, rinsed and transferred into an organ cell containing Tyrode solution, with a content of atropine, kept at a temperature of 34° C. The aeration of the cell is provided by an air compressor.

The sub-maximal concentrations of agonist are determined beforehand on the organ.

The agonist is left in contact with the organ for 20 seconds and the application of agonist is repeated every 2 minutes.

The antagonist is left in contact with the organ for 2 minutes and the agonist, added back to the medium, is again left in contact for 20 seconds.

The experiments are then repeated every 2 minutes until return to normal is achieved.

One experiment is always carried out with the solvent of the tested product as a control.

(b) In the case of the duodenums, the agonist is left in contact for 30 seconds and the time intervals between each treatment are 5 minutes.

(c) The antiserotonin effect was carried out on the isolated uterus of virgin female rats weighing about 200 g. The animal is sensitised with a dose of 1 mg/kg of diethyl stilbestrol administered subcutaneously, and the uterus is then removed and placed in JALON liquid containing a powder which generates carbon dioxide. The dose of serotonin in the cell varies from 0.5 to 2 μg/1 ml. The contact time is the same as that for the duodenum experiments (using the same apparatus and the same process).

The results have been listed in Table II, in which the doses of extracts are expressed as weight (mg) of plant starting material.

Antispasmodic action "in vivo"

The method and the apparatus are those proposed by Konzett and Rossler. The animal used for the experiment is an anaesthetized guinea pig kept under artificial respiration by means of a tracheal cannula. The pump is regulated so as to provide a known volume of air, greater than that which the animal admits, and the excess air escaping through a side-channel is measured. Bronchoconstriction reduces the amount of air admitted and hence manifests itself in an increase in the excess volume of air. In a first stage, the minimum amount of histamine which produces a measurable bronchospasm is determined. Thereafter, in a second stage, the products to be studied are injected

ANALEPTIC RESPIRATORY ACTIVITY

The spontaneous respiration in male guinea pigs, weighing 400–600 g, which have been anaesthetized, is recorded by means of a tracheal probe connected to an electronic recorder.

In a first stage, the respiration is depressed by an intravenous injection of 10 mg/kg of morphine. In a

TABLE II

| Agonist | Dose introduced | Antagonist | Dose introduced | % inhibition |
|---|---|---|---|---|
| Histamine | 0.2 μg/0.5 ml | C-63 | 50 mg/1 ml | 10 |
| Histamine | 0.2 μg/0.5 ml | C-63 | 100 mg/1 ml | 15 |
| Histamine | 0.2 μg/0.5 ml | C-63 | 200 mg/1 ml | 40 |
| Histamine | 0.4 μg/0.5 ml | C-6302 | 16 μg/1 ml | 10 |
|  |  | Dry extract dissolved in a 10:90, volume/volume, mixture of ethanol and water | 160 μg/1 ml | 37 |
|  |  |  | 1,600 μg/1 ml | 56 |
| Histamine | 0.4 μg/0.5 ml | C-63-JA | 1,000 μg/1 ml | 50 |
| BaCl$_2$ | 0.5 mg/0.5 ml | C-63-JA | 20,000 μg/1 ml | 50 |
| Acetylcholine | 0.5 μg/0.5 ml | C-63-JA | 5,000 μg/1 ml | 50 |
| Serotonin | 1 μg/1 ml | C-63-JA | 1,800 μg/1 ml | 50 |
| Histamine | 0.4 μg/.05 ml | C-63-E undiluted | 60 mg/1 ml | 68.5 |
| Histamine | 0.4 μg/0.5 ml | C-63-E dilution ½ | 30 mg/1 ml | 25.9 |
| Histamine | 0.4 μg/0.5 ml | C-63-E dilution ¼ | 15 mg/1 ml | 4.7 |
| Acetylcholine | 1 μg/0.1 ml | C-63-E undiluted | 60 mg/1 ml | 17.8 |
| BaCl$_2$ | 0.5 mg/0.5 ml | C-63-E undiluted | 60 mg/1 ml | 23.8 | venously 1 minute before the histamine.

The percentage inhibition of the bronchospasm is calculated taking into account the amplitude of the bronchospasm or of comparison animals which receive water and the amplitude of the bronchospasm of animals treated with the "C-63" and "C-63-E" extracts, in accordance with the equation:

$$\% \text{ inhibition} = 100 \times \frac{\text{Amplitude of the bronchospasm of the comparison animals} - \text{Amplitude of the bronchospasm of the treated animals}}{\text{Amplitude of the bronchospasm of the comparison animals}}$$

The results (which each represent the mean of 10 measurements) are listed in Table III, in which the doses of extracts are expressed as the weight (mg) of plant starting material.

TABLE III

| Extract | dose in mg/kg administered intravenously | % inhibition of the bronchospasm caused by histamine |
|---|---|---|
| C-63 | 1,250 | 48% |
| C-63 | 2,500 | 69% |
| C-63 | 5,000 | 100% |
| C-63-E | 600 | 55.3% | second stage, 20 minutes after the morphine, the product to be studied is injected intravenously.

The respiratory rhythm is recorded before the injection of morphine, and before and 1 minute after the injection of the product to be studied. The results are listed in Table IV, where theophylline is used as the reference product, and in which the extract doses are expressed as weight of plant starting material.

Anti-anaphylactic activity "in vitro"

Guinea pigs are each given 2 ml of ovalbumin containing 100 mg/ml; 1 ml is administered intraperitoneally and 1 ml is administered subcutaneously. The sensitivity of the animals is increased by an injection of 10 mg in 2 ml, 4 days after the first administration. Three weeks after the last administration, the ileum is removed and placed in a Tyrode bath as indicated above for the study of the antispasmodic effect. The ileum is then placed in contact for 2 minutes with a dose of extract C-63-F1 obtained from 80 mg of plant. 0.2 ml of ovalbumine at a concentration of 1 mg/ml is then added. The reduction caused by C-63-F1 in the amplitude of the contractions produced by

TABLE IV

| Product | dose | respiratory rhythm before morphine | respiratory rhythm 20 minutes after morphine | respiratory rhythm 1 minute after administration of the product |
|---|---|---|---|---|
| C-63 | 5 g/kg given intravenously | 90 pulsations/minute | 47 pulsations/minute | 83 pulsations/minute |
| C-63 | 2.5 g/kg given intravenously | 90 pulsations/minute | 47 pulsations/minute | 65 pulsations/minute |
| C-63-E | 0.3 g/kg given intravenously | 43 pulsations/minute | 29 pulsations/minute | 43 pulsations/minute |

TABLE IV-continued

| Product | dose | respiratory rhythm before morphine | respiratory rhythm 20 minutes after morphine | respiratory rhythm 1 minute after administration of the product |
|---|---|---|---|---|
| C-63-JA | 16 mg/kg given intravenously | 58 pulsations/minute | 29 pulsations/minute | 55 pulsations/minute |
| theophylline | 20 mg/kg given intravenously | 58 pulsations/minute | 29 pulsations/minute | 47 pulsations/minute | ovalbumin is measured. At the dose of 80 mg (which is expressed in terms of the plant), C-63-F1 is found to reduce the contractions due to ovalbumin by 96%.

In general, the therapeutically active products which are extracts of Teucrium marum are C-63, C-63-E, C-63-E1, C-63-E2, C-63-E3, C-63-F1, C-6302 and C-63-JA. Extract C-63-JA is the most valuable in therapy as an antispasmodic and respiratory analeptic agent, for the treatment of spasms and respiratory allergies. C-6302 and C-63-F1 are also valuable but to a lesser degree than C-63-JA.

In clinical practice, C-63-JA has given good results in man in the treatment of respiratory allergies, by the nasal administration, in the form of an aerosol, of a dose of 1 mg/kg/day (that is to say about 200 mg of plant/kg/day) for 3 to 7 days.

According to the invention, a therapeutic compositon is proposed which is in particular useful in the treatment of spasms and respiratory allergies and which is characterised in that it contains, in association with a physiologically acceptable excipient, at least one extract according to the invention at a dose which is pharmaceutically acceptable both in human medicine and in veterinary medicine.

The compositions according to the invention can be administered orally in the form of dragées, capsules, pills, syrups and potable ampoules, locally, especially in the form of ointments or by inhalation and atomising, and rectally, in the form of suppositories or rectal capsules. These compositions can also be administered by injection, especially intramuscular injection, using injectable ampoules.

We claim:

1. A process for the preparation of an extract of Teucrium marum, which process comprises extracting at least a portion of the stems, leaves, floral apices, fruit, or roots of the Teucrium marum plant with a solvent chosen from the group consisting of boiling water in the presence of $NH_3$, pentane, hexane, heptane, cyclohexane, cyclopentane, petroleum ether, methylene chloride and mixtures thereof and purifying the resulting extract, the purified extract having antispasmodic therapeutic activity.

2. A process according to claim 1 wherein one litre of solvent is used for 30 to 150 g of ground and dried plant.

3. A process according to claim 2 wherein the ground and dried plant is treated with boiling water in the presence of $NH_3$ at a rate of 4 to 10 g of $NH_3$ per litre of water.

4. A process according to claim 2 wherein the solvent is hexane.

5. A process according to claim 1 wherein 30 to 150 g of plant are treated under reflux for at least two hours with one litre of water in the presence of 4 to 10 g of $NH_3$, and the resulting aqueous solution is collected by filtration.

6. A process according to claim 1 wherein 30 to 150 g of plant are treated under reflux for at least two hours with one litre of water in the presence of 4 to 10 g of $NH_3$, the resulting aqueous solution is collected, and the following steps are carried out successively:
   (a) the aqueous solution is subjected to absorption on ion exchange resin and the fraction not absorbed is discarded;
   (b) the resin is washed with distilled water until the water is colourless;
   (c) the washed resin is eluted with a solvent chosen from the group consisting of the $C_1$-$C_3$ alkanols and mixtures of these with water which contain at least 90% by volume of lower alkanol, until the eluate is colourless;
   (d) the alkanol-treated resin is eluted with a solvent chosen from the group consisting of the $C_1$-$C_3$ lower alkanols and mixtures of these with water which contain at least 90% by volume of lower alkanol, in the presence of an alkaline agent until the eluate, which is collected, is colourless; and
   (e) the eluate obtained in stage (d) is evaporated in vacuo.

7. A process according to claim 6 wherein the residue from evaporation in stage (e) is purified by successive:
   (f) treatment with diethyl ether to collect the ether phase which is concentrated in vacuo at a temperature less than or equal to 30° C;
   (g) absorption on silica of the concentrate;
   (h) elution with a mixture of hexane and ether (90:10 v/v) of the silica; and
   (i) evaporation to dryness in vacuo of the resulting eluate.

8. A process according to claim 1 wherein the plant is treated by steam stripping at a rate of 30 to 150 g of plant per litre of water in the presence of 4 to 10 g of $NH_3$ per litre of water.

9. A process according to claim 1 wherein the plant is treated by steam stripping at a rate of 30 to 150 g of plant per litre of water in the presence of 4 to 10 g of $NH_3$ per litre of water, and the resulting condensate is subjected to a purification comprising successively;
   rectification at 98° C. under a pressure of 1 atmosphere to collect the distillate;
   extraction with diethyl ether and collection of the ether phase which is concentrated in vacuo at a temperature which is less than or equal to 30° C.;
   absorption on silica of the concentrated ether phase;
   elution with a mixture of hexane and ether (90:10 v/v) of the silica; and
   evaporation to dryness in vacuo of the resulting eluate.

10. A process according to claim 1 wherein the plant is treated with a solvent chosen from the group consisting of pentane, hexane, heptane, cyclopropane, cyclohexane, petroleum ether and mixtures thereof, at a rate of 30 to 150 g of plant per litre of solvent, the extract is filtered and the filtrate is collected and evaporated to dryness in vacuo, and the residue from evaporation is subjected to a purification comprising successively:

treatment of the residue with hexane at a rate of 1 volume of hexane per 10 volumes of initial solvent and collection of the hexane phase;

absorption of the hexane phase on silica;

elution of the silica with a mixture of hexane and ether (90:10 v/v); and evaporation to dryness under reduced pressure of the eluate.

11. A process according to claim 10 wherein the solvent for extraction of the plant is hexane, and the ether in the mixture of hexane and ether is diethyl ether.

12. An extract of *Teucrium marum* prepared according to the process of claim 10, and exhibiting (i) three absorption bands at 2,700–3,000 $cm^{-1}$, 1,700–1,730 $cm^{-1}$ and 1,380–1,460 $cm^{-1}$ in its infra-red spectrum, and (ii) an Rf of 0.45 by chromatography on a thin layer of silica.

13. An extract of *Teucrium marum* obtained according to the process of claim 1.

14. An antispasmodic and analeptic composition which comprises a physiologically acceptable excipient and a pharmaceutically effective amount of at least one extract of *Teucrium marum* according to claim 12.

* * * * *

UNITED STATES PATENT AND TRADEMARK OFFICE
CERTIFICATE OF CORRECTION

PATENT NO. : 4,151,278
DATED : April 24, 1979
INVENTOR(S) : JACQUES DEBAT ET AL

It is certified that error appears in the above–identified patent and that said Letters Patent are hereby corrected as shown below:

Column 8, line 16, change "Antispasmodicaction" to
-- Antispasmodic action --.

Column 14, Claim 12, last line, after the word "silica" insert
-- [mobile phase: chloroform; developer: sulphuric acid-vanillin (1 g of vanillin per 100 ml of $H_2SO_4$ of density 1.84)] --; Claim 14, last line, change "claim 12" to
-- claim 13 --.

Signed and Sealed this

Twenty-fifth Day of September 1979

[SEAL]

Attest:

Attesting Officer

LUTRELLE F. PARKER
Acting Commissioner of Patents and Trademarks